United States Patent
Downs

(10) Patent No.: US 9,623,259 B2
(45) Date of Patent: Apr. 18, 2017

(54) LIGHT BASED INFLAMMATION AND PAIN MANAGEMENT DEVICE

(71) Applicant: Ronald K. Downs, Mishawaka, IN (US)

(72) Inventor: Ronald K. Downs, Mishawaka, IN (US)

(*) Notice: Subject to any disclaimer, the term of this patent is extended or adjusted under 35 U.S.C. 154(b) by 253 days.

(21) Appl. No.: 13/851,489

(22) Filed: Mar. 27, 2013

(65) Prior Publication Data

US 2013/0274836 A1 Oct. 17, 2013

Related U.S. Application Data

(60) Provisional application No. 61/616,212, filed on Mar. 27, 2012.

(51) Int. Cl.
| | |
|---|---|
| A61N 5/06 | (2006.01) |
| A61B 18/18 | (2006.01) |
| A61F 7/02 | (2006.01) |
| A61B 18/20 | (2006.01) |
| A61F 7/00 | (2006.01) |

(52) U.S. Cl.
CPC ............ *A61N 5/0613* (2013.01); *A61F 7/02* (2013.01); *A61B 18/203* (2013.01); *A61F 2007/0045* (2013.01); *A61F 2007/0071* (2013.01); *A61F 2007/0086* (2013.01); *A61F 2007/0087* (2013.01); *A61F 2007/0096* (2013.01); *A61F 2007/0285* (2013.01); *A61N 5/0601* (2013.01); *A61N 5/062* (2013.01); *A61N 2005/0642* (2013.01); *A61N 2005/0652* (2013.01); *A61N 2005/0659* (2013.01); *A61N 2005/0662* (2013.01)

(58) Field of Classification Search
CPC ............ A61N 5/062; A61N 2005/0652; A61N 5/0601; A61B 18/203
USPC ................................................. 607/88; 606/9
See application file for complete search history.

(56) References Cited

U.S. PATENT DOCUMENTS

| | | | |
|---|---|---|---|
| 6,450,941 B1 * | 9/2002 | Larsen ..................... | A61N 1/40 600/14 |
| 6,471,716 B1 * | 10/2002 | Pecukonis ........................ | 607/89 |
| 2002/0029071 A1 * | 3/2002 | Whitehurst .......... | A61N 5/0613 607/88 |
| 2005/0143793 A1 * | 6/2005 | Korman ............... | A61N 5/0616 607/94 |

(Continued)

OTHER PUBLICATIONS

Definition of Ellipse. Merriam-Webster Dictionary, retrieved on Apr. 26, 2016; Retrieved from the Internet: <http://www.merriam-webster.com/dictionary/ellipse>.*

(Continued)

*Primary Examiner* — Lynsey Crandall
*Assistant Examiner* — Sebastian X Lukjan
(74) *Attorney, Agent, or Firm* — Vedder Price, P.C.

(57) ABSTRACT

A portable pain treatment device including a base portion having a first plurality of light emitting devices and a first heating unit on a bottom surface, an upper portion positioned on the end of the base portion opposite the bottom surface, the base portion including an opening, a second plurality of light emitting devices and a second heating unit positioned on an inner surface of the opening, and a control unit configured to control the light intensity of the first and second plurality of light emitting devices and the heat intensity of the first and second heating units.

8 Claims, 3 Drawing Sheets

(56) References Cited

U.S. PATENT DOCUMENTS

| | | | | |
|---|---|---|---|---|
| 2007/0156208 A1* | 7/2007 | Havell | ............. | A61N 5/0616 |
| | | | | 607/88 |
| 2007/0260296 A1* | 11/2007 | Porter et al. | ............. | 607/88 |
| 2009/0005839 A1* | 1/2009 | Griffith | ............. | A61N 5/0614 |
| | | | | 607/91 |
| 2012/0116274 A1* | 5/2012 | Grasso, IV | ............. | 602/2 |
| 2012/0150265 A1* | 6/2012 | Vargas et al. | ............. | 607/91 |
| 2012/0303100 A1* | 11/2012 | Pryor et al. | ............. | 607/90 |
| 2013/0274839 A1* | 10/2013 | Johnson et al. | ............. | 607/90 |

OTHER PUBLICATIONS

Definition of Opening. Merriam-Webster Dictionary, retrieved on Apr. 26, 2016; Retrieved from the Internet: <http://www.merriam-webster.com/dictionary/opening>.*

* cited by examiner

LIGHT BASED INFLAMMATION AND PAIN MANAGEMENT DEVICE

RELATED APPLICATIONS

This application is a non-provisional application that claims the benefit of and the priority from U.S. Provisional Application No. 61/616,212, filed Mar. 27, 2012, titled "LIGHT BASED INFLAMMATION AND PAIN MANAGEMENT DEVICE"

BACKGROUND OF THE INVENTION

The present invention relates generally to a medical device which utilizes light therapy in the treatment of muscle pain and inflammation.

Low level light therapy (LLLT) is used to treat muscle pain caused by inflammation. It is believed that LLLT relieves pain by stimulating muscles to increase vascular activity allowing immune cells to more effectively repair injured or tight muscles. LLLT is presently used to treat a host of ailments including back pain, torn or injured muscles, carpel tunnel syndrome, and other muscle ailments.

Typically, LLLT treatments are performed in a physician's office using a gallium arsenide or gallium aluminum arsenide laser operating at a bandwidth of between 632.8 nm to 904 nm. Several portable LLLT treatment devices have also been developed. However, the portable versions of the LLLT treatment devices only cover a small area of the body, and only operate at a single wavelength. Further, these devices typically require a user to support the weight of the devices in their hand, which may further exasperate muscle pain and discomfort.

While each of these procedures provide varying levels of success in relieving muscle pain, these procedures are performed using very expensive equipment in a physician's office, or using portable units with very limited coverage areas. Accordingly, a need exists for a portable, simple to use device which will allow for relief from muscle pain and other muscle ailments without requiring long treatment durations or a visit to a physician's office.

BRIEF SUMMARY OF THE INVENTION

A portable pain treatment device including a base portion having a first plurality of light emitting devices and a first heating unit on a bottom surface, an upper portion positioned on the end of the base portion opposite the bottom surface, the base portion including an opening, a second plurality of light emitting devices and a second heating unit positioned on an inner surface of the opening, and a control unit configured to control the light intensity of the first and second plurality of light emitting devices and the heat intensity of the first and second heating units.

Other systems, methods, features, and advantages of the present invention will be or will become apparent to one with skill in the art upon examination of the following figures and detailed description. It is intended that all such additional systems, methods, features, and advantages be included within this description, be within the scope of the invention, and be protected by the accompanying claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

Figure 1:
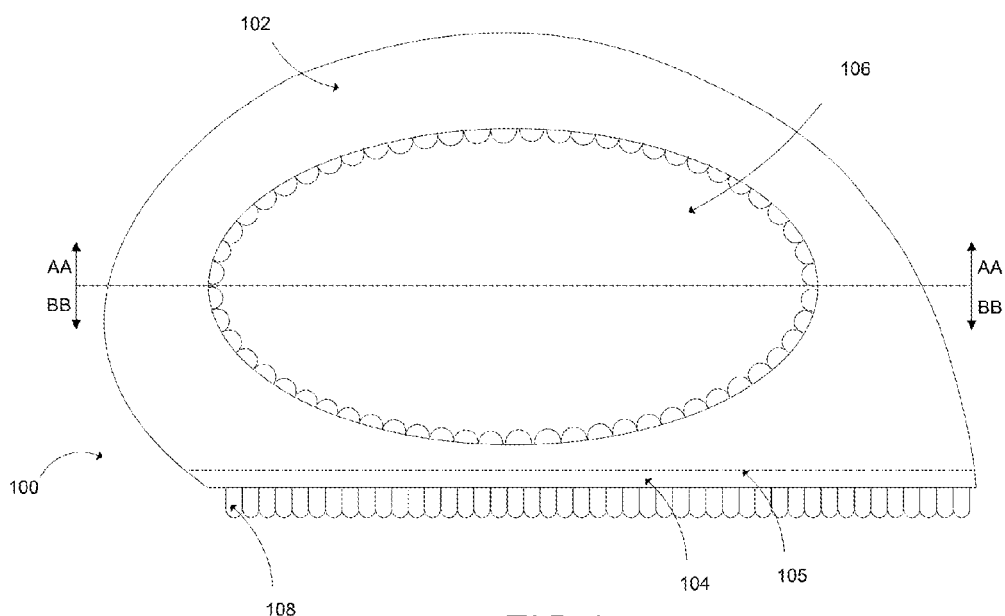
FIG. 1 depicts a side view of a light treatment device.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description of the Invention," relates to a requirement of the United States Patent Office, and does not imply, nor should be inferred to limit the subject matter disclosed herein.

FIG. 1 depicts a side view of a light treatment device 100. The device 100 includes a handle 102 that is separated from a lower portion 104 by an opening 106. The handle 102 may extend from the lower portion 104 in a substantially arc shape. The bottom surface of the lower portion 104 of the device 100 is covered with a plurality of light emitting devices 108. The opening 106 may be substantially elliptical, and may be sized to accommodate a human hand or a foot. The inside surface of the opening 106 also includes a plurality of light emitting devices 110. In another embodiment, only one portion of the inside surface may have a plurality of light emitting devices 110. The light emitting devices 108 and 110 may be light emitting diodes (LED).

Figure 2:
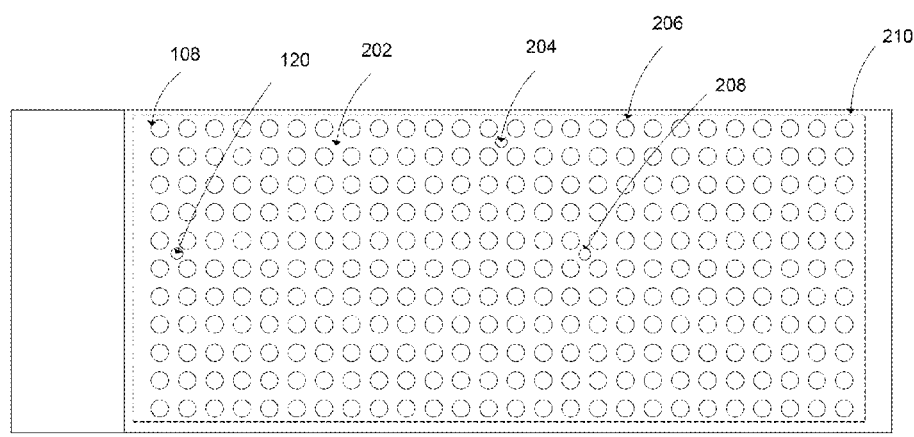
FIG. 2 depicts a bottom view of the device of FIG. 1.

FIG. 2 depicts a bottom view of the device 100. The bottom surface of the device 100 includes the plurality of light emitting devices 108 arranged in a matrix on the lower surface of the device 100. Each light emitting device 108 is configured to emit light in a spectrum ranging from approximately 590 nm to approximately 880 nm. The light emitting devices 108 may be arranged around the periphery of the lower portion 104 or may be equally spaced across the first surface 104 of the handle 102. The light emitting devices 108 may be light emitting diodes ("LED"). Each of the light emitting devices 108 are electrically coupled to a power supply (not shown). The power supply may include a conventional power cord configured to electrically couple to a 120 or 208 VAC power outlet, a battery or any other power source capable of providing power to a light emitting devices 108. Each of light emitting devices 108 are configured to generate a predefined wavelength of light. The predefined wavelength may be between approximately 590 nm and approximately 880 nm.

A heat plate 202 is positioned around the plurality of light emitting devices 108. The heat plate 202 is configured to provide radiant heat to the surface receiving treatment by the device 100. The heat plate 202 is heated by a heating element 210 positioned between the heat plate 202 and the bottom surface of the device. The heating element 210 is capable of heating the heat plate 202 to a predetermined temperature. An insulation layer may be positioned between the heating element 210 and the bottom surface of the device 100 to prevent the bottom surface of the device 100 from being damaged when the heating element 210 is active.

The heat plate 202 may be mounted over the heating element 210. The heat plate 202 may be configured to uniformly distribute the heat generated by the heating element 210. The heat plate 202 may be manufactured from a thermal conducting metal including, but not limited to, copper, steel, stainless steel or any other metal or metal alloy capable of conducting heat. A first surface of the heat plate 202 may be in contact with the skin of the user while a second surface of the heat plate is in contact with the heating element 210. The heating element 210 may also be incorporated into the heat plate 202 The heat plate 202 may also be separated from the surface of the skin by a predefined distance.

The heat plate 202 may include at least one surface temperature sensor 204 that is capable of reading the temperature of the surface receiving treatment. The temperature sensor 204 may be a contactless infrared temperature sensor, a thermistor, a thermocouple, or any other device capable of reading the temperature of the surface of an object. More than one temperature sensor 204 may be arrayed between the light emitting devices 108 on the bottom surface of the device 100. The heat plate 202 may also be positioned around the periphery of the bottom surface of the device 100.

The heat plate 202 may also include at least one light level sensor 208 that is capable of reading the amount of light generated by the light emitting devices 108. The light level sensor 208 may be any sensor capable of detecting the amount of light generated by the light emitting devices 108 and converting the amount of light into an electrical signal. More than one light level sensor may be arrayed between the light emitting devices 108 on the bottom surface of the device 100.

The heat plate 202 includes a plurality of openings 206 that correspond to the light emitting devices 108 when the heat plate 202 is positioned on the upper portion 104 of the device 100. The openings 206 are sized to each accommodate at least one light emitting device 108. The heat plate 202 may also be configured such that an upper portion of each light emitting device 108 is substantially flush with a top surface of the thermally conducting plate 112. A thermally conductive fluid may be applied to the skin of the user to enhance the operation of the heating element 210. The thermally conducting fluid assists in the uniform transfer of heat from the heat plate 202 to the surface of the skin.

Figure 3A:
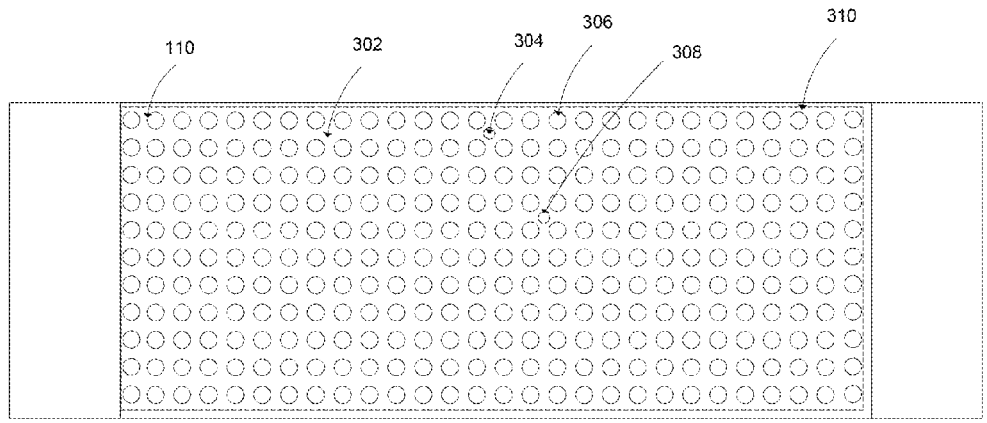
FIG. 3A depicts a cut away view of the device along lines AA depicting the inner surface of the handle of the device of FIG. 1.
Figure 3B:
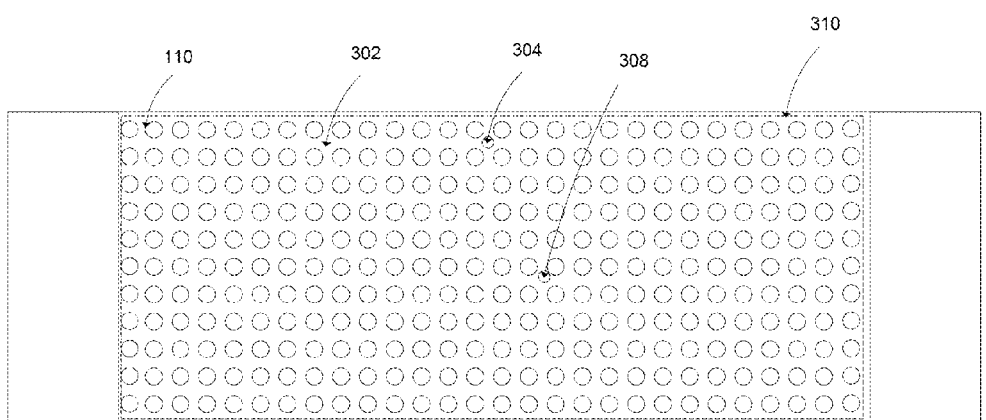
FIG. 3B depicts a cut away view of the handle of the device of FIG. 1 along the lines BB.

FIG. 3A depicts a cut away view of the device along lines AA, depicting the inner surface of the handle 104 of the device 100, and FIG. 3B depicts a cut away view of the handle 102 of the device 100 along the lines BB. The inner surface of the handle 102 includes a plurality of light emitting devices 110 arranged in a matrix. Each light emitting device 110 is configured to emit light in a spectrum ranging from approximately 590 nm to approximately 880 nm. A heat plate 302 is positioned around the plurality of light emitting devices 110. The heat plate 402 is configured to provide heat to the surface receiving treatment by the device 100 in the same manner as the heat plate 202 on the bottom surface of the device. A heating element 310 is positioned The heat plate 302 may include at least one surface temperature sensor 304 that is capable of reading the temperature of the surface receiving treatment. The temperature sensor 304 may be a contactless infrared temperature sensor, a thermistor, a thermocouple, or any other device capable of reading the temperature of the surface of an object. More than one temperature sensor 304 may be arrayed between the light emitting devices 110 on the inner surface of the handle 102. The heat plate 302 may also be positioned around the periphery of the handle 102.

The heat plate 302 is heated by a heating element 310 positioned between the heat plate 302 and the bottom surface of the device. The heating element 310 is capable of heating the heat plate 302 to a predetermined temperature. An insulation layer may be positioned between the heating element 310 and the bottom surface of the device 100 to prevent the bottom surface of the device 100 from being damaged when the heating element 310 is active.

The heat plate 302 may also include at least one light level sensor 308 that is capable of reading the amount of light generated by the light emitting devices 110. The light level sensor 308 may be any sensor capable of detecting the amount of light generated by the light emitting devices 110 and converting the amount of light into an electrical signal. More than one light level sensor may be arrayed between the light emitting devices 110 on the bottom surface of the handle 102.

The heat plate 302 includes a plurality of openings 306 that correspond to the light emitting devices 108 when the heat plate 302 is positioned on the upper portion 104 of the device 100. The openings 306 are sized to each accommodate at least one light emitting device 108. The heat plate 302 may also be configured such that an upper portion of each light emitting device 108 is substantially flush with a top surface of the thermally conducting plate 112. A thermally conductive fluid may be applied to the skin of the user to enhance the operation of the heating element 310. The thermally conducting fluid assists in the uniform transfer of heat from the heat plate 202 to the surface of the skin.

Figure 4:
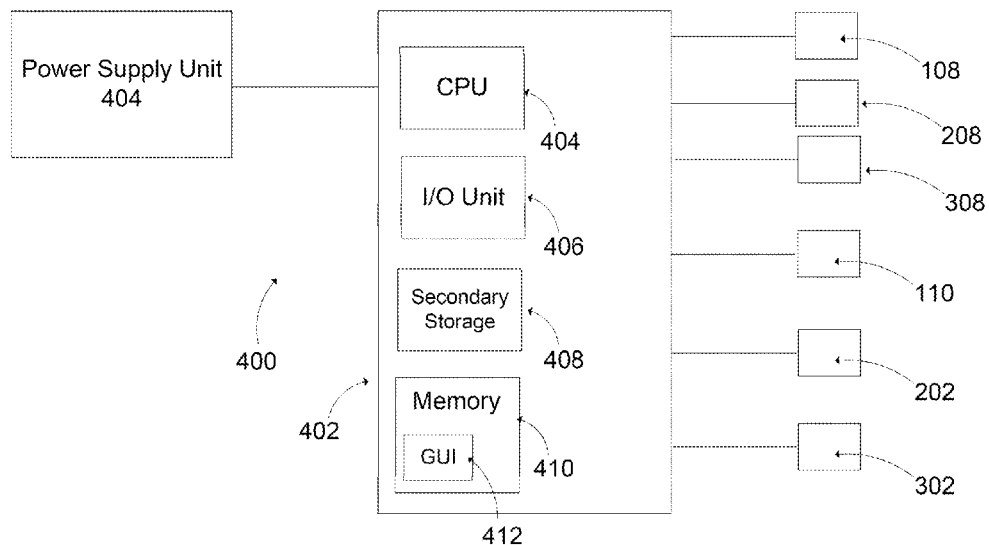
FIG. 4 depicts one embodiment of a control panel used to control the light emitting device of FIG. 1.

FIG. 4 depicts one embodiment of a control panel 400 used to control the device 100. The control panel 400 includes a central control unit 402 that is electrically coupled to each of the light emitting devices 108 and 110 and the heating plates 202 and 302. The central control unit 402 includes a central processing unit (CPU) 404, an input output (I/O) unit 406, a secondary storage device 408, and a memory 410. Central control unit 402 may further comprise standard input devices such as a keyboard, a mouse, a digitizer, or a speech processing means (each not illustrated). The I/O unit 406 may further include a plurality of analog outputs which provide a variable voltage or current to the heating elements 210 and 310 and the light emitting devices 108 and 110. The I/O unit 406 also includes a plurality of inputs electrically coupled to sensors, such as temperature sensors 204 and 304, which monitor environmental conditions related to the operation of the device.

In one embodiment, the central control unit 402 includes a Graphical User Interface ("GUI") 412 in the memory 410 which is used to display information via a display device connected to the I/O unit 406 as described herein. The GUI 412 includes any user interface capable of being displayed on a display device including, but not limited to, a web page, a display panel in an executable program, or any other interface capable of being displayed on a computer screen. Further, the GUI 412 may also be stored in the secondary storage unit 408.

The central control unit 402 is electrically coupled to a power supply 404. The power supply 404 can be any type of power supply unit capable of providing adequate power to the light emitting devices 108 and 110, and the heating plates 202 and 302. In one embodiment, the power supply unit 404 is an electrical plug that is connected to a 120 or 208 VAC power outlet. In another embodiment, the power supply unit 404 is a battery such as, but not limited to, a Lithium Ion Battery, a Nickel Cadmium battery, or any other battery type capable of simultaneously powering the heating plates 202 and 302 and the light emitting devices 108 and 110.

In one embodiment, the control unit 402 is electrically coupled to each of the light emitting devices 108 and 110 individually. In another embodiment, the control unit 402 is electrically coupled to groups of light emitting devices 108 and 110. The control unit 402 is configured to vary the power supplied to each of the light emitting devices 108 and 110 such that the total wavelength of all of the light emitting devices 108 and 110 is between approximately 590 nm and 880 nm. The control unit 402 may be electrically coupled to a light level sensors 208 and 308 via the IO unit, which transmits the total light level emitted from the light emitting devices 108 and 110 to the control unit 402. The light level sensors 208 and 308 may be positioned on a surface of the heat plates 202 and 302 such that the light level sensors 208 and 308 read the amount of light generated by the respective light emitting devices 108 and 110 surrounding each light level sensors 208 and 308. Additional light level sensors 208 and 308 may be positioned on the surface of the heating plates 202 and 302 and coupled the control unit 402 via the I/O unit 406. Consistent with this embodiment, software operating in the CPU 404 of the control unit 402 modulates the power to each light emitting device 108 and 110 individually, or in groups, to maintain a constant light level output form the device 100.

The control unit 402 allows for independent operation of the light emitting devices 110 in the handle and the light emitting devices 108 on the bottom surface of the device 100. A user interface on the device may allow a user to select different treatment options such as pain management or other modes. Based on the mode selected by the user, the control panel 402 will modulate the light level intensity and heat intensity based on the treatment selected. The user interface may be a liquid crystal display (LCD) panel communicatively coupled to the I/O unit 406 of the control unit 402. The user interface may include a plurality of dials and buttons that allow a user to configure different light and heat intensity settings.

The control unit 402 also provides power to the heating plates 202 and 302 via an analog output on the I/O unit 406 of the control unit 402. Software operating in the CPU 404 of the control unit 402 modulates the heating plates 202 and 302 such that the heating plates 202 and 302 do not exceed a predefined temperature setpoint. The control unit 402 may monitor the amount of heat generated by, or the amount of power transmitted to, the heating plates 202 and 302 to maintain the predefined setpoint. The control unit 402 may also monitor the surface temperature of the skin and modulate the heat output from the heating plates 202 and 302 to maintain a constant surface temperature.

The control unit 402 may also store treatment programs in the memory 410 that modulate the light intensity and heat levels of the treatment over time. The LCD panel may also gather information from a user of the device to further adjust how the device operates. As an illustrative example, the device may have a treatment schedule targeted at reducing pain in a patient's hands over a period of time. The treatment program may be loaded into the memory 410 of the control unit 402 via the LCD or external software. The treatment program may by based on the number of times a user has received treatment, such as generating one level of light intensity and heat the first treatment and increasing the level over a predetermined number of treatments. The treatment program may also vary the heat and light intensity over the duration of a single treatment.

After a treatment cycle in the treatment program is completed, the control unit 402 may request pain level information from the user. As an illustrative example, the control unit 402 may prompt the user to rate their pain level before and after treatment. The control unit 402 may vary the treatment program based on the user input. As an illustrative example, the control unit 402 may increase the intensity of the light and heat until the user indicates a downward trend in their pain. When the downward trend in pain is sensed, the light and heat intensity may be adjusted.

Consistent with this embodiment the surface temperature sensors 204 and 304 are used to measure the temperature of the skin. The surface temperature sensor may include, but is not limited to, an IR sensor, a thermistor, a RTD sensor or any other temperature sensor capable of measuring the surface temperature of human skin. In one embodiment, the predefined skin surface temperature is approximately 192 degrees Fahrenheit/89 degrees Celsius.

In another embodiment, the operation of the heating plates 202 and 302 is enhanced by incorporating a thermally conductive fluid between the skin and each heating unit 202 and 302. The thermally conducting fluid assists in the uniform transfer of heat from the heating plates 202 and 302 to the surface of the skin. The thermally conducting fluid may be a heat activated silicone treatment patch, or cream, impregnated with antioxidants such as vitamins A, C, and E. The patch may also include Potassium iodide. When the heat activated patch is used, the heat plates 202 and 302 will heat the surface to at least the activation temperature of the patch or cream. The activation temperature of the patch or cream may be stored in the memory 410 of the control panel 402. Further, the presence of the patch or cream may by indicated via the display panel coupled to the control panel 402.

In another embodiment, the control unit 402 includes an imaging device, such as a camera, coupled to I/O unit 406 which captures images of the area being treated by the device. The imaging device 120 may be a digital camera positioned in an opening in the thermal plate 112. The imaging device 120 may be any known digital imaging device 120 including a CCD digital camera, a SLR digital camera, or any other known imaging device 120. The imaging device 120 includes a memory, a processor, and an image sensor, such as a CCD or CMOS sensor. The imaging device 120 may be coupled to the control unit 402 via a data connection such as, but not limited to a fire wire connection, a USB connection, or any other data connection. To capture an image, the control unit 402 illuminates the region using the light emitting devices 108 before capturing an image of the area covered. Once the image is captured, it is stored along with user information and a date/time in the storage unit 408. The images may be captured before or after treatment.

In one embodiment, the control unit 402 includes a communication unit configured to transmit the captured images to at least one computer connected to the communication unit via a network. The network is of a type that is suitable for connecting the computers for communication, such as a circuit-switched network or a packet-switched network. The network may include a number of different networks, such as a local area network, a wide area network such as the Internet, telephone networks including telephone networks with dedicated communication links, connectionless network, and wireless networks. Consistent with this embodiment, the transmitted images can be used by the user or a physician to track the progress of treatment.

In another embodiment, the control unit 402 stores the skin temperature readingss, light level readings, operating temperatures of the heater and images of the treatment area over time in a treatment storage unit in the secondary storage 408. Consistent with this embodiment, the control unit 402 transmits the data to a second computer or display device via the I/O unit. In another embodiment, the control unit 402 includes an external port which allows the data in the secondary storage unit to be transferred to an external storage device.

Figure 5:
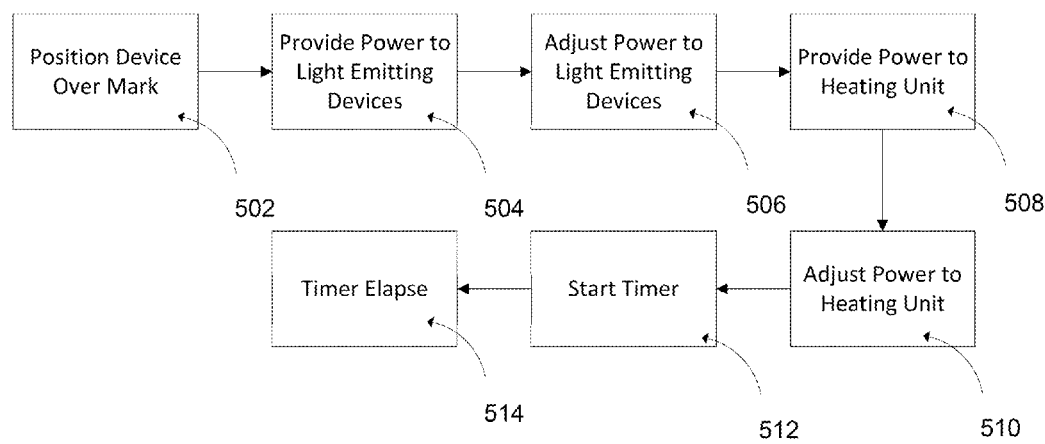
FIG. 5 depicts a method of treating pain and inflammation using the pain management device.

FIG. 5 depicts a method of treating pain and inflammation using the pain management device 100. In step 502, the device is positioned over a portion of the body experiencing pain such that the light emitting devices 106 and heating element 210 or 310 are opposite the surface of the skin. Alternatively, the portion of the body may be inserted into the opening 106 in the handle 102. In other words, the light emitting devices 106 and heating element 210 or 310 face the surface of the skin. In step 504, the control unit 402 triggers an output to provide power to the plurality of light emitting elements 106. In step 506, the control unit 402 adjusts the power provided to each light emitting elements 108 or 110 until a signal from a light level sensor 208 or 308 indicates that the light emitting elements 108 or 110 are producing light at a predetermined intensity.

In step 508, the control unit 402 triggers an output providing power to the heating element 210 or 310. In step 510, the control unit 402 adjusts the current provided to the heating element 210 or 310 in response to a temperature signal from a temperature sensor. Alternatively, the control unit 402 may simultaneously provide power to the light emitting elements 108 and 110 and the heating element 210 or 310. In step 512, the control unit 402 initiates a timer that maintains the temperature and intensity setpoints for a predetermined period of time. In step 514, the control unit 402 turns off the heating element 210 or 310 and the light emitting elements 108 and 110 when the timer elapses.

Because the device 100 is portable, patients can effectively utilize the device 100 at home without having to travel to a physician for costly and expensive conventional treatments.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A portable pain treatment device comprising:
A housing;
A lower portion including a bottom surface of the housing, wherein the bottom surface comprises: a first plurality of light emitting devices and a first heating unit;
A handle portion which extends from the lower portion of the device and wherein said handle portion is separated opposite from the lower portion of the device by an elliptical shaped upper opening;
The elliptical shaped opening further comprising:
An inner surface enclosed between the handle portion and the lower portion of the housing with the inner surface having a periphery that is sized to accommodate an arm or a foot and wherein the entire periphery of the inner surface includes a second plurality of light emitting devices and a second heating unit;
A control unit configured to control the light intensity of the first and second plurality of light emitting devices and the heat intensity of the first and second heating units.

2. The portable pain treatment device of claim 1 including a power supply unit in the device that is configured to provide power to the light emitting devices, the heating units, and the control unit.

3. The portable pain treatment device of claim 1, wherein the control unit separately controls the light intensity of the first plurality of light emitting devices and the second plurality of light emitting devices.

4. The portable pain treatment device of claim 1, wherein the first plurality of light emitting devices are configured to emit a light having a wavelength of between approximately 590 nm and 880 nm.

5. The portable pain treatment device of claim 1, wherein the light intensity of the first or second plurality of light emitting devices is determined based on a treatment program stored in a memory of the control unit.

6. The portable pain treatment device of claim 1, wherein the light intensity and heat intensity of the first plurality of light emitting devices and the first heating unit is based on a pain level intensity gathered by the control unit from a user.

7. The portable pain treatment device of claim 1, wherein the light intensity and heat intensity of the second plurality of light emitting devices and the second heating unit is based on a pain level intensity gathered by the control unit from a user.

8. The portable pain treatment device of claim 1, wherein the control unit generates light from the light emitting devices simultaneously with the generation of heat from the heating units.

* * * * *